(12) United States Patent
Weill et al.

(10) Patent No.: US 9,308,057 B2
(45) Date of Patent: Apr. 12, 2016

(54) EJECTION DEVICE FOR EJECTING SMALL DOSES

(75) Inventors: David Weill, Begnin (CH); Pierre-Yves Chassot, Thoiry (FR)

(73) Assignee: Primequal SA, Geneva (CH)

( * ) Notice: Subject to any disclaimer, the term of this patent is extended or adjusted under 35 U.S.C. 154(b) by 0 days.

(21) Appl. No.: 13/515,120

(22) PCT Filed: Dec. 9, 2010

(86) PCT No.: PCT/EP2010/069278
§ 371 (c)(1),
(2), (4) Date: Jun. 11, 2012

(87) PCT Pub. No.: WO2011/070122
PCT Pub. Date: Jun. 16, 2011

(65) Prior Publication Data
US 2012/0248152 A1 Oct. 4, 2012

(30) Foreign Application Priority Data
Dec. 9, 2009 (FR) ...................... 09 58814

(51) Int. Cl.
| B67D 7/60 | (2010.01) |
| G01F 11/00 | (2006.01) |
| A61C 5/06 | (2006.01) |
| A61M 5/315 | (2006.01) |

(52) U.S. Cl.
CPC ............ *A61C 5/062* (2013.01); *A61M 5/31586* (2013.01); *A61M 2005/3152* (2013.01)

(58) Field of Classification Search
CPC ..... G01F 11/00; G01F 11/025; G01F 11/026; G01F 11/027; G01F 13/00; B65D 83/11; A61M 5/31583; A61M 5/31586; A61M 2005/3152; A61C 5/062
USPC .................... 222/390, 391; 604/61, 207–211; 74/575–578; 254/222; 401/65, 66
See application file for complete search history.

(56) References Cited

U.S. PATENT DOCUMENTS 1,416,614 A * 5/1922 Cournand ...................... 604/155
1,581,836 A * 4/1926 Brown .......................... 222/320

(Continued)

FOREIGN PATENT DOCUMENTS

DE 100 15 616 A1 3/2000
FR 1318748 A * 1/1962

(Continued)

OTHER PUBLICATIONS

FR 1318748 A—English Translation.*

(Continued)

*Primary Examiner* — J. Casimer Jacyna
*Assistant Examiner* — Benjamin R Shaw
(74) *Attorney, Agent, or Firm* — Frommer Lawrence & Haug LLP

(57) ABSTRACT

The invention relates to a device for ejecting a liquid or paste product, including a body (2) having a recess (11) for receiving a product to be ejected, characterized in that it includes a threaded rod (3), which is translatably movable so as to act on the product to be ejected, a bolt (5), which is mounted so as to engage with the threaded rod (3) in order to cause same to translatably move, and a lever (1) acting on the bolt (5) by means of a control means for causing the rotation thereof.

16 Claims, 8 Drawing Sheets

(56) References Cited

U.S. PATENT DOCUMENTS

| | | | |
|---|---|---|---|
| 1,718,596 A * | 6/1929 | Smith | 604/223 |
| 4,865,231 A * | 9/1989 | Wiercinski | 222/390 |
| 4,994,029 A * | 2/1991 | Rohrbough | 604/88 |
| 5,375,740 A * | 12/1994 | Umetsu et al. | 222/95 |
| 5,573,341 A * | 11/1996 | Iaia | 401/172 |
| 5,647,515 A * | 7/1997 | Zwijnenberg et al. | 222/389 |
| 6,464,663 B1 * | 10/2002 | Zinger | 604/82 |
| 6,716,198 B2 * | 4/2004 | Larsen | 604/207 |
| 7,169,132 B2 * | 1/2007 | Bendek et al. | 604/208 |
| 7,195,616 B2 * | 3/2007 | Diller et al. | 604/224 |
| 2007/0131721 A1 * | 6/2007 | Fritschi et al. | 222/391 |
| 2008/0243087 A1 * | 10/2008 | Enggaard et al. | 604/208 |
| 2010/0105003 A1 | 4/2010 | Weill et al. | |
| 2012/0095412 A1 * | 4/2012 | Schabbach et al. | 604/211 |

FOREIGN PATENT DOCUMENTS

| | | | |
|---|---|---|---|
| FR | 2913341 A1 | | 3/2007 |
| GB | 2064012 A | * | 6/1981 |
| JP | 03240678 A | * | 10/1991 |
| WO | WO 2008/107813 A1 | | 9/2008 |

OTHER PUBLICATIONS

FR 1318748 A—English Translation, Jan. 13, 2014.*
French Search report in support of the French priority document.

* cited by examiner

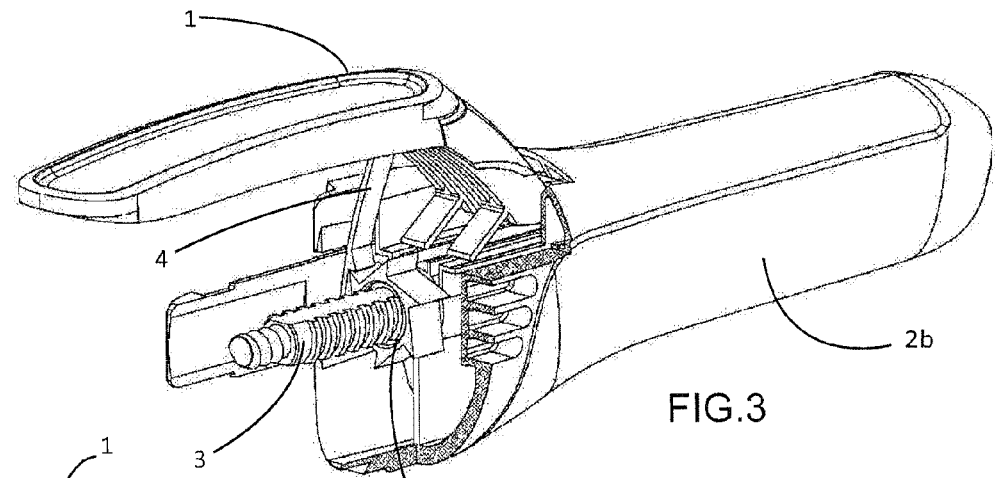
FIG.3
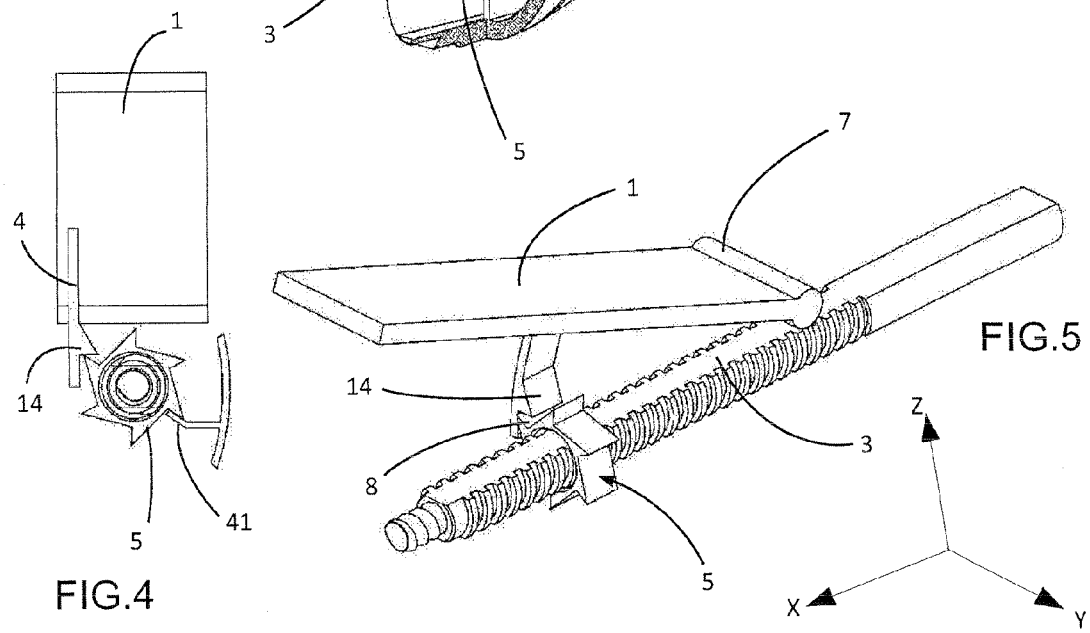
FIG.4
FIG.5
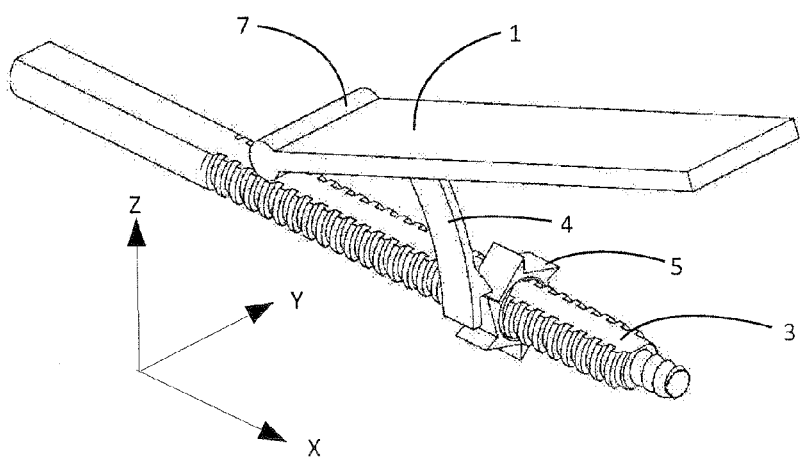
FIG.6

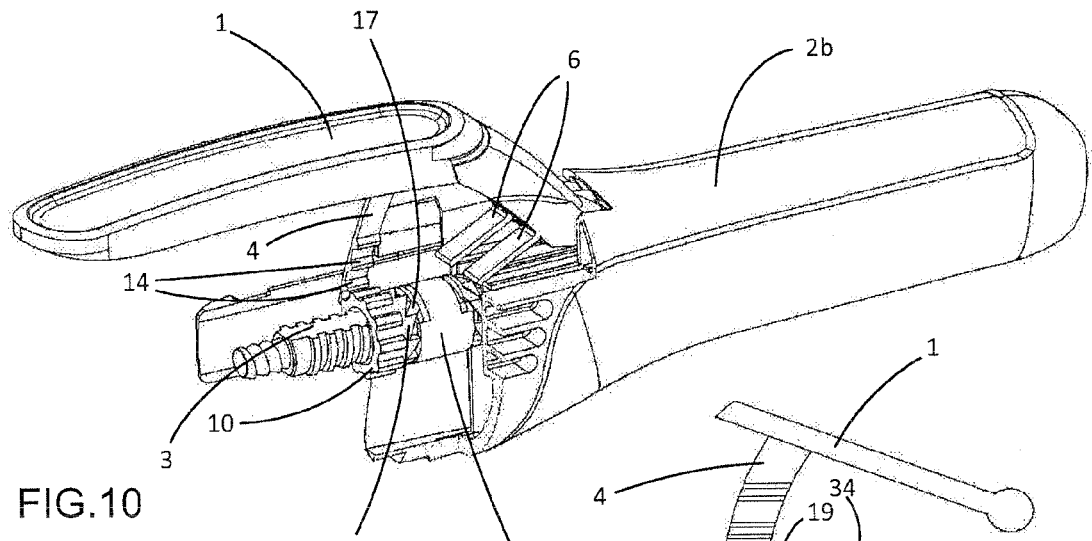
FIG.10
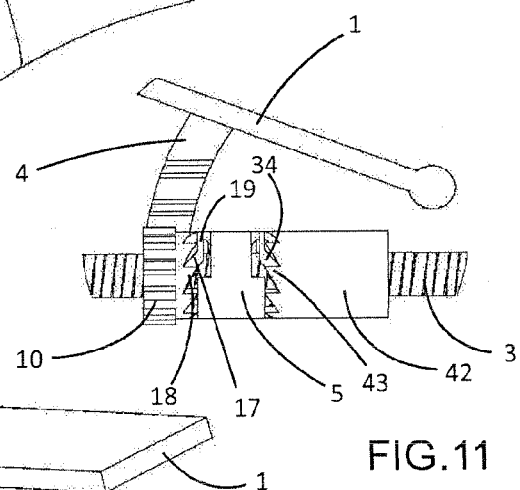
FIG.11
FIG.12
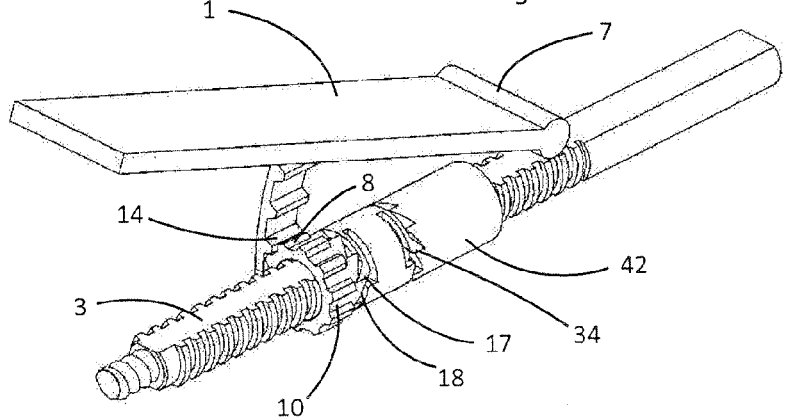
FIG.13

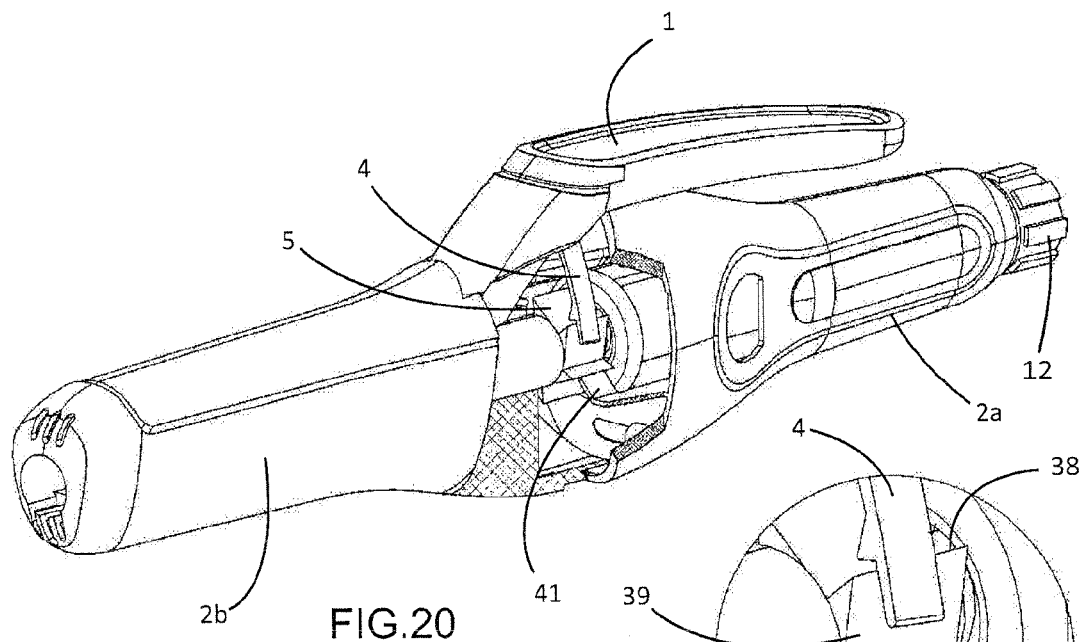
FIG.20
FIG.21
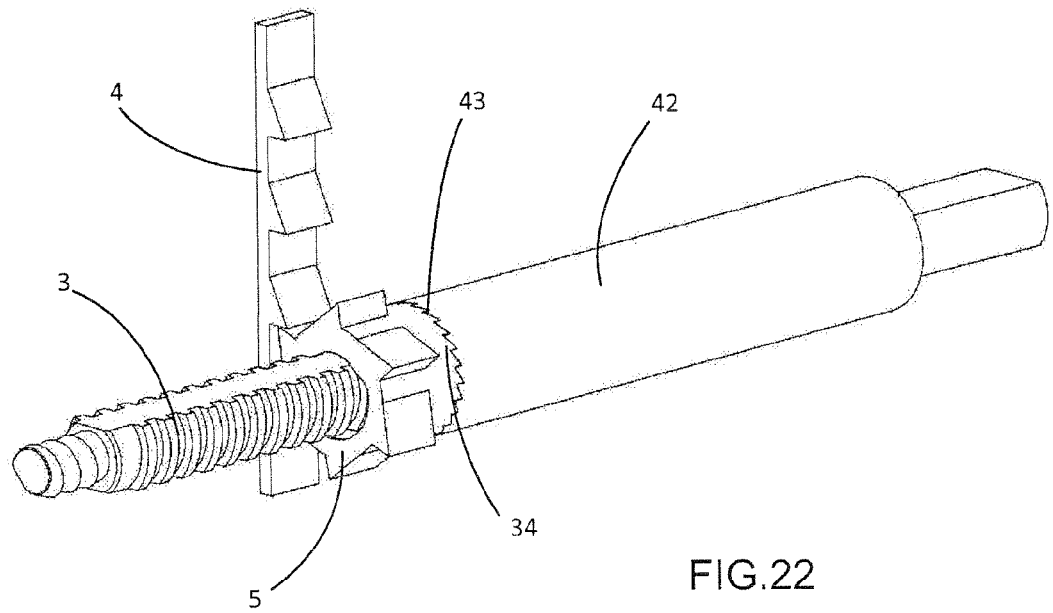
FIG.22

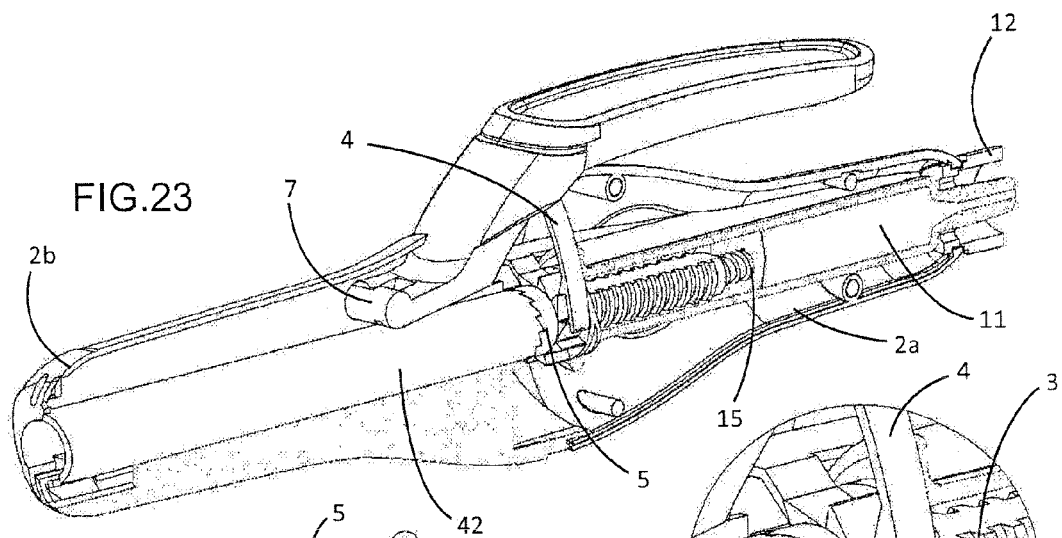
FIG. 23
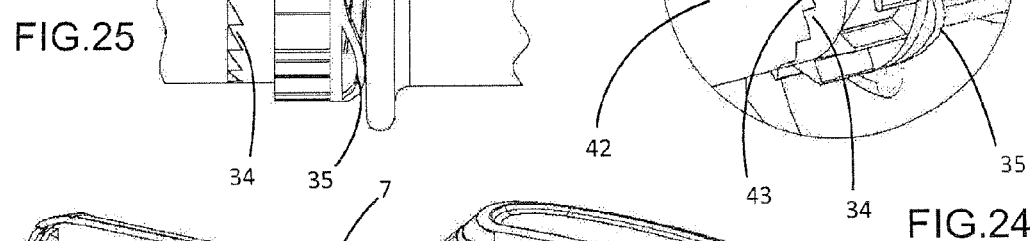
FIG. 25
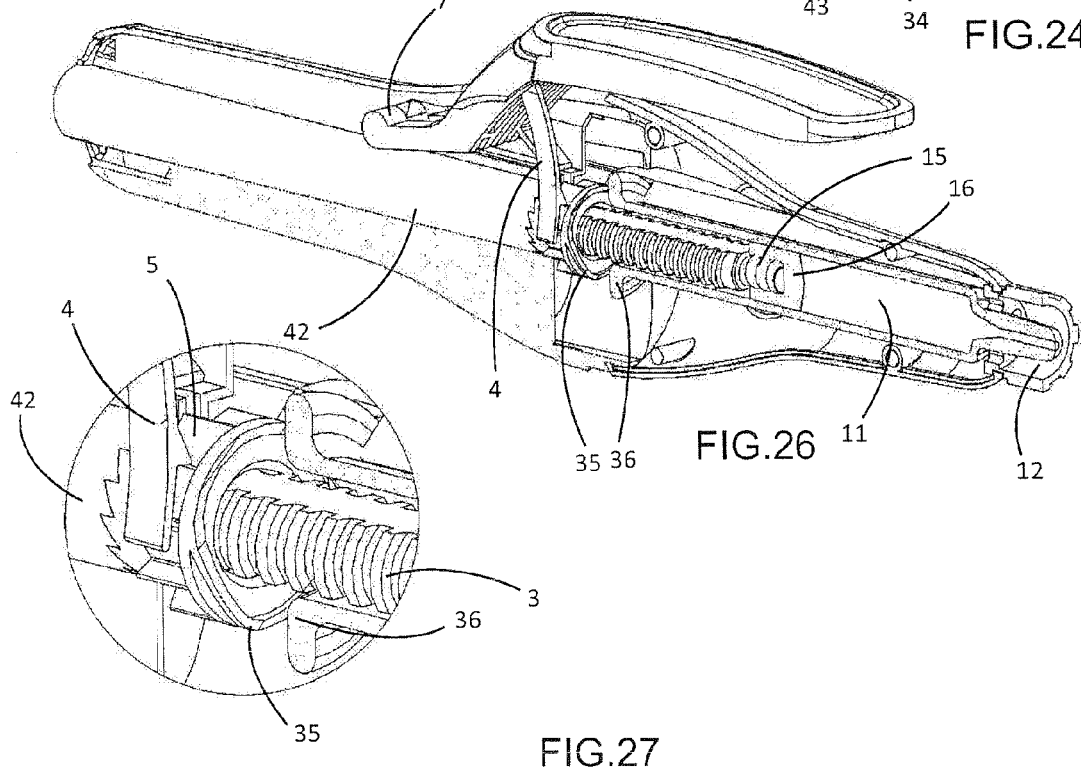
FIG. 24
FIG. 26
FIG. 27

EJECTION DEVICE FOR EJECTING SMALL DOSES

This application is a 371 of PCT/EP2010/069278 filed on Dec. 9, 2010, published on Jun. 16, 2011 under publication number WO 2011/070112 A1, which claims priority benefits to French Patent Application 0958814 filed Dec. 9, 2009, the entire disclosure of which is incorporated herein by reference.

The invention relates to a device for ejecting a liquid or pasty product.

A conventional and very simple device designed for ejecting a product, and used particularly in the fields of medicine and dentistry, takes the form of a rectilinear and substantially cylindrical syringe comprising a front cartridge containing the product to be ejected and a cylindrical and rectilinear rear piston, which is movable in translation inside the cartridge. An operator simply pushes the piston, which slides inside the cartridge, ejecting the product through the front end of the cartridge on which a needle is mounted. The manufacture of such a syringe meets stringent demands in respect of hygiene and sterility, especially as regards the integration of the product in the cartridge. A disadvantage of this solution stems from the fact that it is difficult to manipulate such a syringe, since pushing the piston is awkward and makes it impossible to control the ejection of a precise dose and to eject the product at a controlled speed. This disadvantage makes it unsuitable for certain areas, such as cosmetic surgery which requires the ejection of small doses with great precision and the use of sometimes thick or even pasty products, such as hyaluronic acid, necessitating a considerable ejection force.

Document WO2008/107813 proposes an ejection device which is of a simpler design and which is easy to dismantle and clean. This device comprises a body, a part which is intended to contain the product and is provided with an orifice for ejection of the product, a toothed pusher cylinder, of the ratchet type, traveling through a bore in the body and varying the volume of the part intended to contain the product, and a mechanism for moving the pusher cylinder connected to the body, comprising a detachable hinged lever which acts on the teeth of the pusher cylinder by way of a pawl connected to the lever. This solution has the advantage of great simplicity and better control of the ejected dose. A minimal ejected dose corresponds to the distance separating two teeth of the pusher cylinder. Such a design reaches its limits when very small doses are needed. This is because a pusher cylinder according to this design cannot generally have more than fifty or so teeth along the push length used, which proves inadequate, especially in cosmetic surgery and in certain dental applications. Furthermore, increasing the number of teeth necessitates reducing their size, which means that the teeth have less hold and the ejection device is less reliable.

Hence, a general object of the invention is to make available a solution for ejecting a liquid or pasty product overcoming the disadvantages of the existing solutions.

More specifically, a first object of the invention is to make available a solution for ejecting a liquid or pasty product by which the ejected dose can be controlled with great precision.

A second object of the invention is to make available a solution for ejecting a liquid or pasty product offering a maximum degree of hygiene.

A third object of the invention is to make available a simple and economical solution for ejecting a liquid or pasty product.

To this end, the invention is based on a device for ejecting a liquid or pasty product, comprising a body having a recess for receiving a product to be ejected, characterized in that it comprises a threaded rod, which is movable in translation so as to act on the product to be ejected, a bolt, which is mounted in engagement with the threaded rod in order to cause the latter to move in translation, and a lever, which acts on the bolt by way of a control means for causing the rotation thereof.

The control means can comprise a pawl connected to the lever.

The lever can be mounted for rotation or flexion about an axle arranged in the rear part thereof. This axle can also be situated at its rear end and can comprise a means for fixing this axle movably on the body of the ejection device.

The lever and the pawl can form the same molded plastic component.

The bolt can comprise teeth or slots engaging directly or indirectly with the pawl, these teeth or slots being arranged on the outer peripheral surface thereof, the profile of the teeth extending in a vertical transverse plane and/or in a vertical longitudinal plane.

The pawl can be in the form of a shaft connected to the lever at a first end, forming an elastically or non-elastically movable shaft, and can comprise a second end able to engage with teeth of a ratchet, comprising a rectangular end and/or one or more teeth toward this second end, or a second end comprising a rounded part able to engage with a slot.

The ejection device can comprise a ratchet mounted in rotation about the threaded rod and comprising several teeth which are arranged on the outer peripheral surface thereof and of which the profile extends in a vertical transverse plane in order to engage with the pawl, and comprising at least one tooth oriented in a longitudinal direction in order to engage with the bolt so as to drive the latter in rotation during the actuation of the lever.

The teeth of the bolt or of the ratchet can have a pointed profile and be asymmetrical or have a rectangular, conical or trapezoid symmetrical profile.

The means for controlling the bolt can comprise one or more intermediate gears for gearing down the transmission of the speed of rotation to the bolt.

The bolt can comprise an alternating sequence of inclined slots and longitudinal slots formed on the outer cylindrical surface thereof.

The ejection device can comprise a pawl connected to the lever, of which one end engages with the slots of the bolt, and/or can comprise, at its end, an actuation element comprising several engagement elements engaging with the slots of the bolt so as to cause the bolt to rotate during the actuation of the lever.

The ejection device can also comprise a non-return device comprising an elastic blade or one or more teeth connected to the body of the device and in engagement with the bolt, in order to form a non-return device for the bolt, preventing reverse rotation thereof when the lever is released.

The non-return device can comprise a cylindrical component formed in the area of the bore in which the threaded rod moves, comprising teeth which extend in a longitudinal direction at one of the ends thereof and which come into engagement with at least one complementary tooth extending in the longitudinal direction of the bolt.

The ejection device can comprise a means for emitting an audible click when a minimal dose is ejected by the actuation of the lever.

The ejection device can comprise a body comprising a front part, containing the product to be ejected, and a separate rear part, containing the bolt.

Finally, it can comprise at least one tool holder arranged in the front part of the body of the ejection device and/or a tool holder arranged in the front part of the body of the ejection device and a locking means of the Luer lock type for locking the tool holder on the ejection device.

These objects, features and advantages, and others, of the present invention are set out in detail in the following description of particular embodiments which are given as non-limiting examples and with reference to the attached figures, in which:

FIG. 3 shows a partial perspective view of an ejection device according to a first variant of the first embodiment of the invention.

FIG. 4 shows a partial view from the front of the ejection device according to the first variant of the first embodiment of the invention.

FIG. 5 shows a perspective view from a first side of the mechanism of the ejection device according to the first variant of the first embodiment of the invention.

FIG. 6 shows a perspective view from the second side of the mechanism of the ejection device according to the first variant of the first embodiment of the invention.

FIG. 10 shows a partial perspective view of an ejection device according to a second embodiment of the invention.

FIG. 11 shows a side view of the mechanism of the ejection device according to the second embodiment of the invention.

FIG. 12 shows a perspective view from a first side of the mechanism of the ejection device according to the second embodiment of the invention.

FIG. 13 shows a perspective view from the second side of the mechanism of the ejection device according to the second embodiment of the invention.

FIG. 20 shows a partial perspective view of an ejection device according to the invention comprising a first embodiment of a non-return device.

FIG. 21 shows an enlarged perspective view of details of this non-return device.

FIG. 22 shows a perspective view of the pusher mechanism of an ejection device according to the invention comprising a second embodiment of a non-return device.

FIG. 23 shows a partial perspective rear view of the ejection device according to the invention comprising the second embodiment of a non-return device.

FIG. 24 shows an enlarged perspective view of details of this non-return device.

FIG. 25 shows a partial side view of the ejection device comprising the second embodiment of a non-return device.

FIG. 26 shows a partial perspective front view of the ejection device according to the invention comprising the second embodiment of a non-return device.

FIG. 27 shows an enlarged perspective front view of details of the ejection device comprising the second embodiment of a non-return device.

Figure 1:
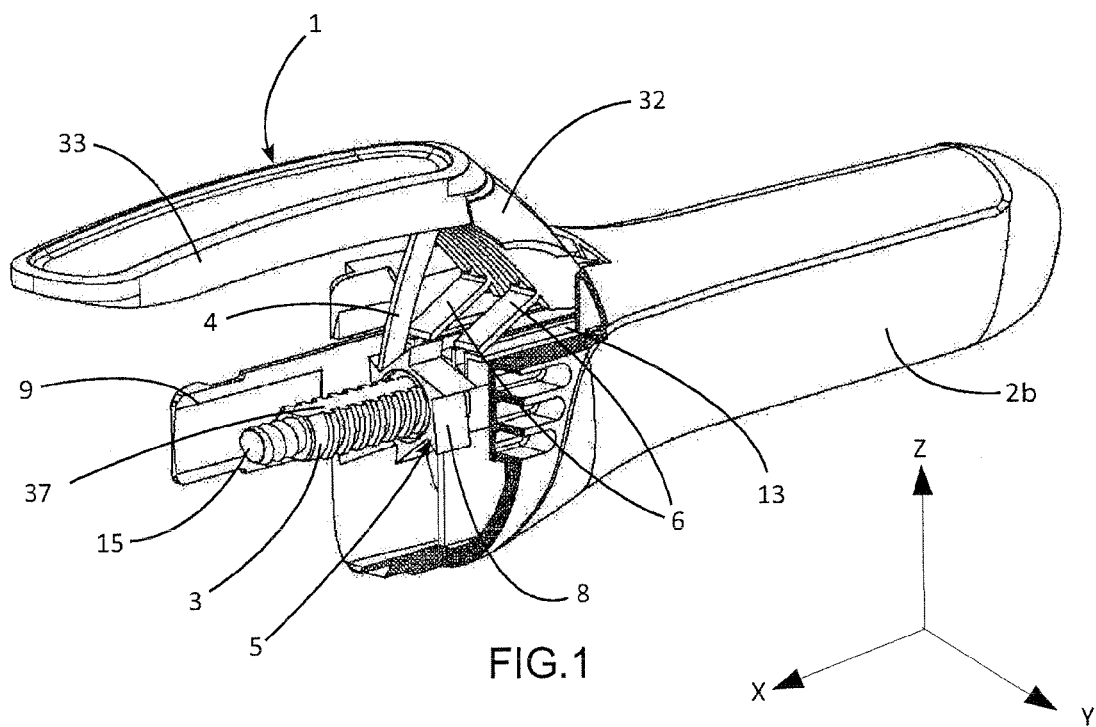
FIG. 1 shows a partial perspective view of an ejection device according to a first embodiment of the invention.

In the following description, x designates the longitudinal axis extending from the rear of the ejection device to the front part thereof, the front part being the end where the product is ejected, z designates the vertical axis perpendicular to the axis x and passing through the middle part of the lever, and y designates the transverse axis perpendicular to the two preceding axes x and z, as is shown in the figures.

The embodiments of the invention will be described in the context of an ejection device serving as a syringe designed for the dental field, for example for injecting a product into the gums, or for cosmetic surgery, for example for injecting a thick gel under the skin. However, the invention can be exploited in other fields for any ejection of a product in the form of a liquid, gel or paste, for example a glue.

For simplicity, the ejection device is shown in part in most of the figures, so as to better illustrate the pusher mechanism to which the invention relates. Moreover, the components that are similar and that have equivalent functions are designated by the same reference sign in the various figures corresponding to different embodiments, despite the fact that their form may vary.

The concept of the invention lies in combining the use of an advantageous lever with a pusher mechanism based on a threaded rod and a bolt. Pressure on the lever permits movement of the threaded rod on the basis of a very simple and reliable control means, as will be described below.

In the preferred embodiments of the invention that are described below, the ejection device is composed of a main body obtained by assembly of separate components, which are advantageously manufactured by plastic injection molding. This main body comprises a front part 2a, which is connected to a rear part 2b by a lateral connection means 9. The front part 2a performs the function of "container vessel" of the body of the device, that is to say it comprises a storage volume 11 of the product to be ejected, while the rear part 2b contains the mechanism permitting the ejection of the product, which will be explained below. The front part 2a can either directly form a volume containing the product to be ejected or can have a site for receiving a separate cartridge that comprises the product to be ejected. The ejection device also comprises, in its front part, a tool holder 12 for receiving a needle (not shown). In most of the figures, the body 2a, 2b is not shown, or shown in part, so as to provide a view of the internal mechanism. Alternatively, the device can directly comprise a front end forming the ejection tool, such as a pipet for ejection of glue, for example, rather than a separate tool holder.

Moreover, the ejection device can comprise a locking device (not shown) of the type known and standardized under the name "Luer lock", which is in the form of a ring fixed around the body of a cartridge so as to prevent detachment of the needle. The reason is that the high pressures exerted on the product for ejecting it are transmitted to the front part of the cartridge, and the tool holder risks being flung forward at high speed like a dart.

Figure 2:
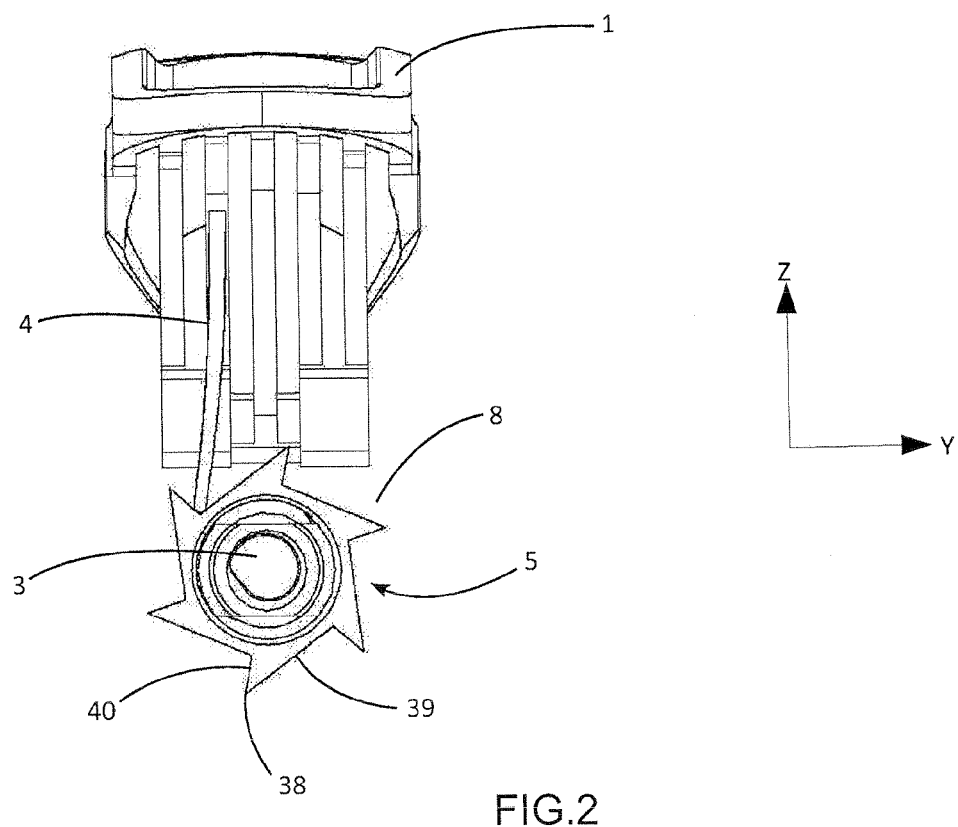
FIG. 2 shows a partial view from the front of the ejection device according to the first embodiment of the invention.

FIGS. 1 and 2 show a first embodiment of the invention, in which an ejection device comprises an ejection mechanism comprising mainly a lever 1, a threaded rod 3, a bolt 5, and a control means between the lever and the bolt.

As in all the embodiments shown, the lever 1 is mounted to rotate on the body of the ejection device about a transverse axle 7 positioned in the front part of the lever. It comprises an inclined part 32 extending from its rounded end forming its axis of rotation 7 to a substantially horizontal part 33 in its rest position intended for its actuation. It also comprises an elastic means 6 whose function, like a spring, is to return the lever to its upper rest position. For this, the elastic means 6 is composed of two elastic blades, of which one end is connected to the lever 1 and the other end bears on a lateral plane part 13 formed inside the body of the device, which comprises a notch in its upper part for the passage of this elastic means 6 and of a pawl 4, of which the function is explained below. Alternatively, the elastic means could have other geometries, for example a single blade. In another variant, this function of the elastic return means can be performed by the pawl 4.

The fastening of the lever on the body of the device could be fixed, and the lever could function by simple flexion of its inclined part 32, by virtue of its elasticity, in a manner equivalent and similar to the effect obtained during its rotation. In such a case, the front axle 7 could, for example, be mounted fixed in position in the body of the ejection device, with no possibility of rotation. To make matters simpler, only the rotation movement of the lever will be considered in the remainder of the description.

A pawl 4 connects the lever 1 to the bolt 5 and has the main function of a means for controlling the rotation of the bolt 5 from the lever 1. It extends downward to the inside of the body 2b, via the upper notch, from the inclined part 32 of the lever 1. It is in the form of a rectangular blade, of which the plane rectangular face is oriented in the transverse direction y. Advantageously, the lever 1, the pawl 4 and the elastic means 6 are obtained in a single plastic molding step, and these three components form just one piece, an integral unit. The flexibility of the plastic material and the form of the connection between, on the one hand, the pawl and the lever and, on the other hand, between the elastic means and the lever permit an elastic movement of the pawl and of the elastic means in relation to the lever. In all the embodiments, the lever could alternatively have other geometries and other types of articulation, without departing from the concept of the invention.

The bolt 5 is mounted movably in rotation around the threaded rod 3. It is positioned in a fixed manner in the longitudinal direction with respect to the ejection device, the body of this device having an internal abutment preventing any advance or retreat of the bolt 5. The latter comprises teeth 8 on its outer peripheral surface, of which the cross section in a plane yz, visible in FIG. 2, has points 38 formed by an asymmetrical tooth profile comprising inclined parts 39 with a gentle slope and parts 40 oriented substantially in a direction transverse to the longitudinal direction x. These teeth 8 of the bolt 5 engage with the lower end of the pawl 4, which takes up a position in abutment between two parts 39, 40 of a tooth 8. Finally, the threaded rod 3 is fixed in rotation and free in translation in a central cylindrical bore of the ejection device. It has a cylindrical shape, of which a part 37 is truncated in order to prevent its rotation, by engagement with a bore of corresponding shape.

The rear of the ejection device is obtained by prior assembly (not shown) of the threaded rod 3 and its bolt 5 with the rear body 2b, by their insertion into this rear body 2b, as far as their position in which the front end 15 of the threaded rod is able to engage with the pusher piston 16 for the product to be ejected, as can be seen particularly in FIGS. 23 and 26. Likewise, there is another preliminary assembly step in which the movable lever 1 is joined to the rear body 2b. The lever 1 comprises a horizontal upper part 33 extending toward the front, and designed to be manipulated, then a downwardly inclined part 32 comprising a rear lower end in the form of an axle 7, which is positioned at a corresponding site of the rear body 2b. Thus, the axis of rotation 7 of the lever 1 is situated toward the rear end of the lever 1, and the pawl 4 extends from the inclined part 32 of the lever as far as the teeth 8, which thus form a ratchet on the outer periphery of the bolt 5. The horizontal upper part of the lever can thus be moved downward, by a rotation of the lever about the axle 7, thereby entraining the pawl 4 bearing against the teeth 8 of the ratchet until causing the rotation of the bolt 5.

Figure 18:
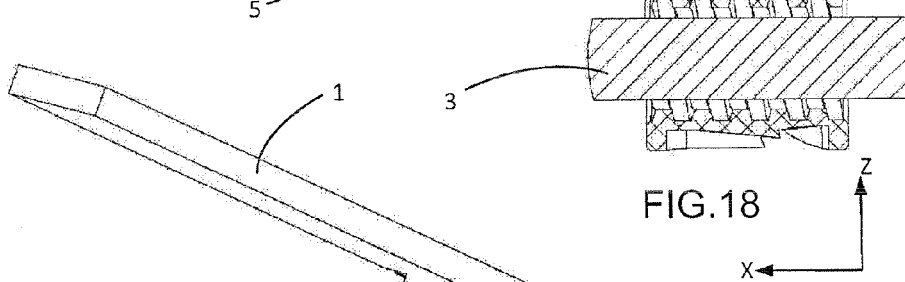
FIG. 18 shows a cross-sectional side view of the fourth embodiment of the invention.

The ejection device function will now be explained. A user acts on the lever 1 by pressing it down, causing it to rotate about its axis of rotation 7. This movement drives down the pawl 4, of which the lower end, positioned in abutment against a tooth 8 of the bolt 5, drives the tooth 8 in its downward movement and thus drives the bolt 5 in rotation. Since the bolt 5 is fixed in the longitudinal direction of the ejection device, its rotation causes the forward longitudinal movement of the threaded rod 3, of which the thread engages with the thread of the bolt 5, as can be seen in FIG. 18. The advance of the threaded rod 3 allows it, by engagement with a front piston 16, to exert a thrust on the storage volume 11 of the product contained in the front body 2a of the device, causing its ejection. When the lever has continued its downward movement toward the body of the ejection device as far as its lowest position, the user releases the lever, which returns automatically to its upper position under the effect of the elastic means 6. At the same time, a non-return means 41, which will be discussed in detail below, prevents any rotation of the bolt 5 in the opposite direction, thereby preventing any rearward longitudinal movement of the threaded rod 3.

During the downward movement of the lever 1, the lower end of the pawl 4 rises, moving slightly away from its natural position by sliding along the inclined slope 39 of the following tooth 8 on the outer surface of the bolt. The teeth 8 have a ramp shape, which promotes this sliding. At the end of the retreat movement of the pawl 4, it reaches the point 38 of the following tooth before lodging itself once again in the abutment formed by the next tooth 8, by an elastic effect of the plastic material used, which brings the pawl 4 back to its substantially vertical original position once the lower end of the pawl passes this point of the next tooth.

The spacing of the various teeth 8 of the bolt 5 corresponds to the clearance of the lever 1, such that the pawl 4 optimally permits actuation of a single tooth for each actuation of the lever 1. In the embodiment shown in FIG. 1, the bolt 5 comprises 6 teeth on its outer surface, allowing it to be rotated by a sixth of a turn on each actuation of the lever. Thus, six actuations of the lever are needed to achieve a complete turn of the threaded rod 3 and, therefore, the longitudinal advance of the latter over a distance defined by a turn of its thread. This solution has the advantage of allowing control of a very small movement of the threaded rod upon actuation of the lever 1, thus making it possible to perfectly control the ejection of small doses of products. Of course, the bolt could comprise a different number of teeth, depending on the required precision and on the required force.

FIGS. 3 to 9 show variants of the first embodiment, having a function similar to that described above, in which a pawl 4 connected to the lever 1 forms the means of controlling the rotation of the bolt 5, which drives the threaded rod 3.

FIGS. 3 to 6 show a first variant of the first embodiment of the invention, in which the pawl 4 comprises a tooth 14 toward its lower end, of a shape engaging with the teeth 8 of the bolt 5. With this variant, it is possible to increase the engagement between the pawl 4 and the bolt 5. This tooth 14 has a profile matching those of the bolt 5, being asymmetrical, so as to promote the movement of the bolt 5 in the ejection phase and non-movement in the phase of ascent of the lever.

Figure 7:
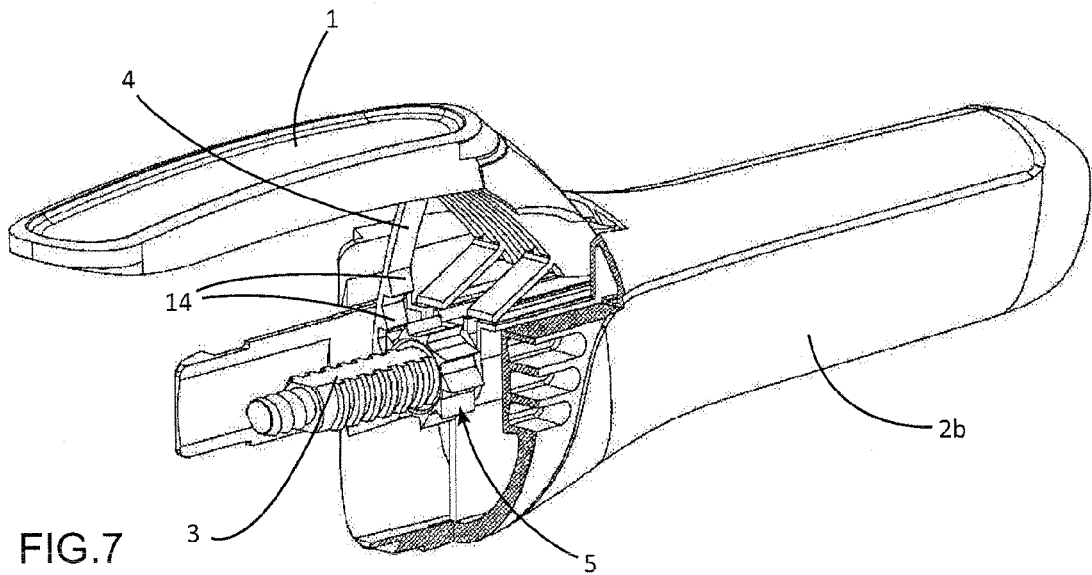
FIG. 7 shows a partial perspective view of an ejection device according to a second variant of the first embodiment of the invention.
Figure 8:
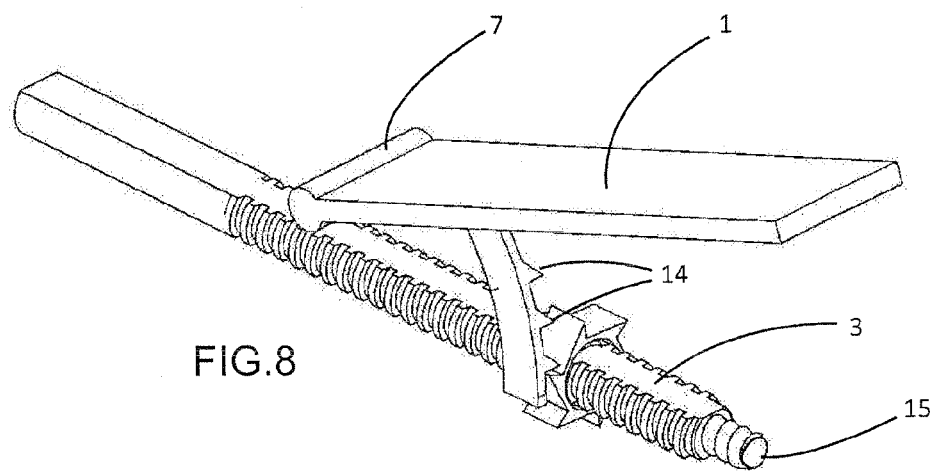
FIG. 8 shows a perspective view from a first side of the mechanism of the ejection device according to the second variant of the first embodiment of the invention.
Figure 9:
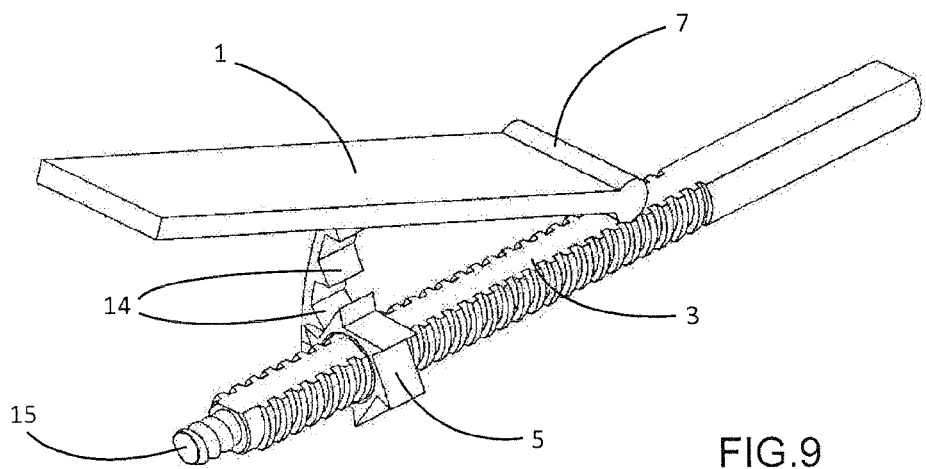
FIG. 9 shows a perspective view from the second side of the mechanism of the ejection device according to the second variant of the first embodiment of the invention.

FIGS. 7 to 9 show a second variant of the first embodiment, in which several teeth 14 are formed at the lower end of the pawl 4. During the downward actuation of the lever 1, different teeth 14 come into successive or simultaneous engagement with teeth 8 of the bolt 5. This solution further reinforces the connection between the pawl 4 and the bolt 5.

FIGS. 10 to 12 show a second embodiment of the invention, in which two different parts, which are positioned around the threaded rod 3, are used to perform the functions of ratchet, on the one hand, and bolt, on the other hand. The lever 1 still in fact comprises a pawl 4 comprising several teeth 14, which come into engagement with a ratchet 10 consisting of a cylindrical part which is movable in rotation around the threaded rod 3 and of which the inner cylindrical surface simply slides on the outer surface of the threaded rod, while its outer cylindrical surface forms a ratchet engaging with the pawl 4. The ratchet 10 moreover comprises a second series of teeth 18, of which the points are oriented in the longitudinal direction and which cooperate with a matching tooth 17 of a separate bolt 5.

During the downward actuation of the lever 1, the pawl 4 drives the ratchet 10 in rotation by virtue of the engagement of their respective teeth 8, 14, similarly to the first embodiment. However, the ratchet 10 simply turns by sliding on the outer surface of the threaded rod 3, without directly driving the rotation of the latter. However, the ratchet 10 comprises complementary teeth 18, which come into engagement with at least one complementary tooth 17 formed on the bolt 5 and positioned in contact with the ratchet 10 around the threaded rod 3. In this way, the rotation of the ratchet 10 in this direction of rotation drives the rotation of the bolt 5, which induces the movement of the threaded rod 3, as has been explained above.

During the downward movement of the lever 1, a tooth 34 of the bolt 5 engages with the teeth 43 of a non-return device 42, in accordance with a function that will be explained in detail below. During this engagement, once the elastically deflected tooth 34 of the bolt escapes from a tooth 43, it finds itself suddenly in its initial rest position by means of an elastic effect and emits an audible click, and the user can tell from this click that a tooth 43 has been passed, which corresponds to a certain precise dose of ejected product. During the downward movement of the lever, one or more audible clicks can be emitted depending on the geometry of the teeth in question.

When the lever rises again, the pawl 4 drives the rotation of the ratchet 10 in the reverse direction around the threaded rod, by the same amplitude as the preceding rotation. In this embodiment, the pawl 4 does not need to deflect elastically during the upward movement of the lever, and this phase is thereby facilitated. The shape of the teeth 17, 18 of the bolt 5 and ratchet 10, respectively, is such that the reverse rotation of the ratchet does not drive the rotation of the bolt. This is because the tooth 17 of the bolt, being formed on an elastic blade 19 of the bolt 5, deflects elastically during the reverse rotation of the ratchet without driving the rotation of the bolt.

In this embodiment, the engagement between the pawl 4 and the ratchet 10 is obtained by teeth with a more symmetrical profile, since the ratchet is driven in the two directions of rotation in a substantially equivalent manner. Thus, the profile of the teeth 8, 14 of the pawl 4 and of the ratchet 10, respectively, can, for example, have a rectangular, conical or trapezoid profile. This embodiment makes it possible to reduce the stresses exerted on the pawl, which only has to deflect from its natural orientation during the upward movement of the lever. In this second embodiment, the means for controlling the bolt 5 thus consists of a pawl 4 and a ratchet 10.

Figure 14:
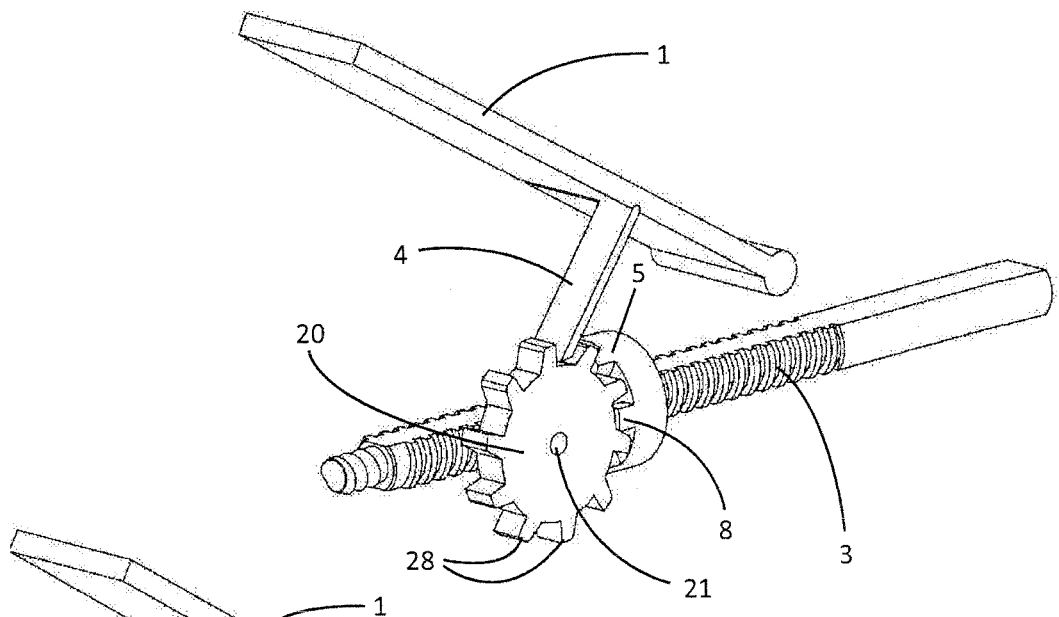
FIG. 14 shows a perspective view of the pusher mechanism of an ejection device according to a third embodiment of the invention.

FIG. 14 illustrates a third embodiment of the invention, in which the means for controlling the bolt 5 uses an intermediate gear 20 in order to gear down the amplitude of rotation finally transmitted to the threaded rod 3. Thus, a pawl 4 has one end which engages with an intermediate gear 20 movable in rotation about a transverse axle 21. The teeth 28 of this gear then engage with teeth 8 extending in a longitudinal direction of the bolt 5. Through its rotation, the latter then transmits a movement of translation to the threaded rod, as has been explained above.

Figure 15:
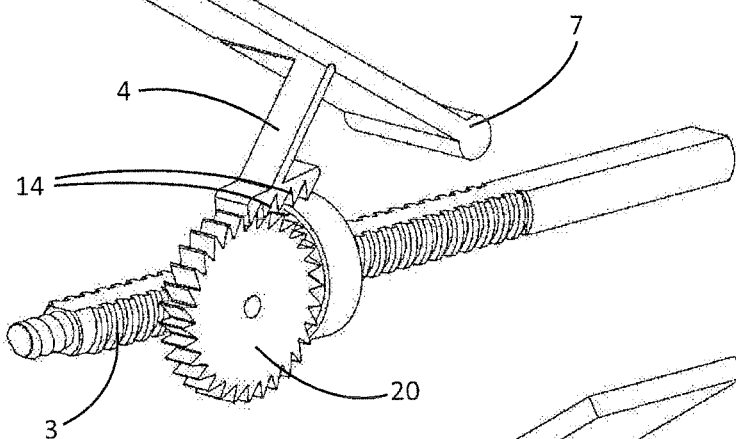
FIG. 15 shows a perspective view of the pusher mechanism of an ejection device according to a first variant of the third embodiment of the invention.

FIG. 15 illustrates a variant of this third embodiment, in which the pawl, at its end, has a flat part extending in the longitudinal direction and comprising several teeth 14, which engage with the teeth of the intermediate gear 20. This geometry permits the use of smaller teeth than before and the engagement of several teeth at the same time.

Figure 16:
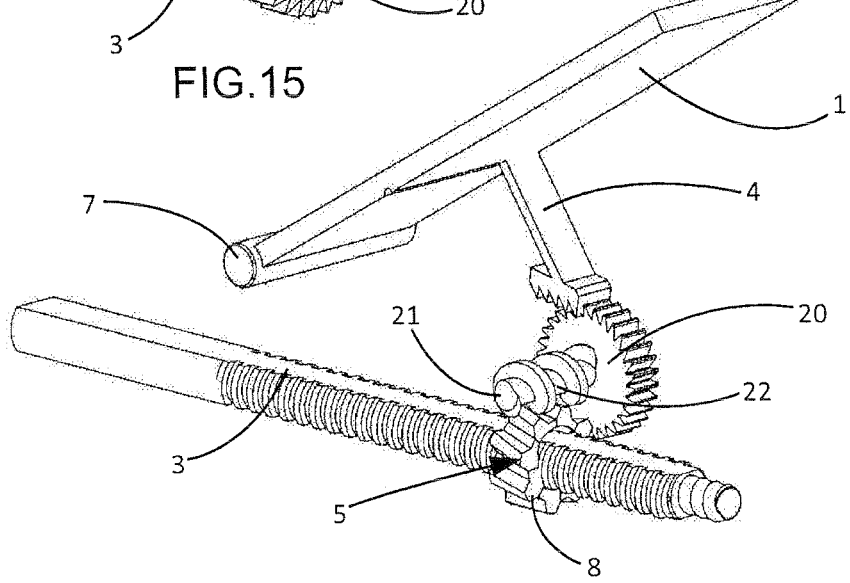
FIG. 16 shows a perspective view of the pusher mechanism of an ejection device according to a second variant of the third embodiment of the invention.

FIG. 16 illustrates a second variant of this third embodiment, in which a second intermediate gear 22 is used which is integral with the first intermediate gear 20, is likewise movable in rotation about a transverse axle 21 and comprises a threaded surface that engages with teeth 8 of the bolt, which teeth 8 are organized on the outer cylindrical peripheral surface but are inclined with respect to the longitudinal direction in order to engage with the thread of the intermediate gear 22.

This third embodiment has the advantage of further refining the movement of translation transmitted to the threaded rod 3 by the actuation of the lever 1 and of permitting the ejection of very small doses at each actuation. It is thus possible to attain a number of actuations of the lever of more than 100 for the ejection of all of the product, which is particularly advantageous for certain applications demanding great precision, such as cosmetic surgery. Of course, many variations of this third embodiment are conceivable in which the means for controlling the bolt comprises a pawl and one or more gears, comprising all kinds of mechanical connection by teeth, cams, etc., and any direction of axis of rotation.

Figure 17:
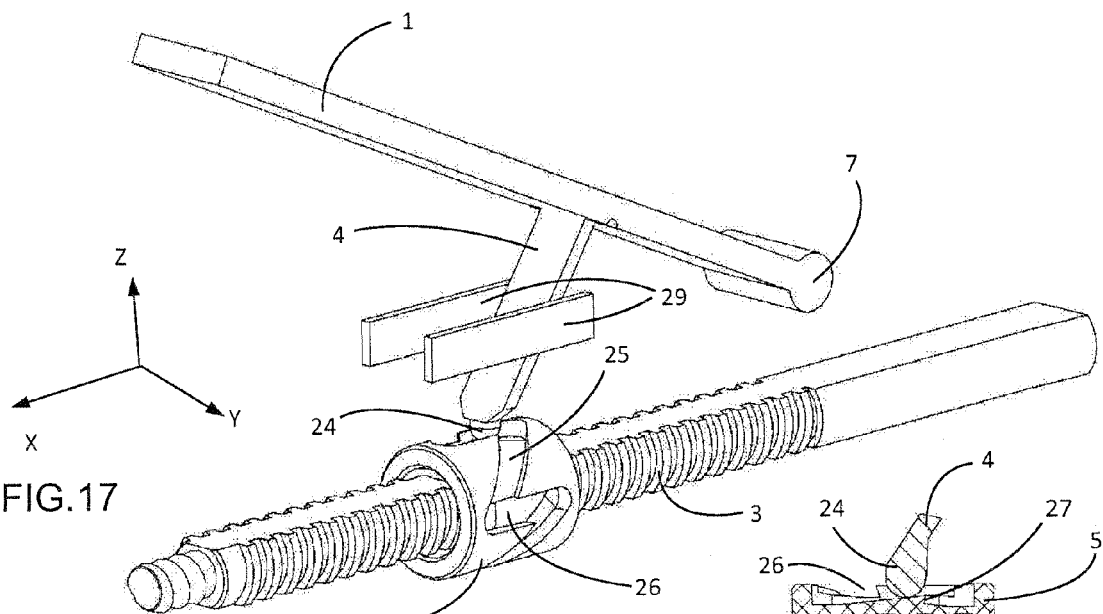
FIG. 17 shows a perspective view of the pusher mechanism of an ejection device according to a fourth embodiment of the invention.

FIGS. 17 and 18 show a fourth embodiment of the invention. The pawl 4 connected to the lever 1 has an end 24 with a rounded shape, such as a hemisphere or ball, which moves inside slots forming cams provided on the outer cylindrical surface of the bolt 5. These slots are provided in a form alternating between slots 25, which are inclined with respect to the longitudinal direction, and slots 26, which are substantially longitudinal. Moreover, the surface at the bottom of these slots form ramps with certain interruptions allowing the end 24 to be held in certain positions, as will be described in detail below.

In the upper position of the lever, the end 24 of the pawl 4 is positioned in the most rearward part of an inclined slot 25. When the user acts on the lever in order to press it down, a pushing force is transmitted to the bolt 5 by the pawl. More precisely, a force with a longitudinal direction is applied by the end 24 on the slot 25, of which the inclination represents a ramp which drives the rotation of the bolt, while the end 24 of the pawl 4 moves along the inclined slot 25. At the end of the travel of the lever, the end 24 of the pawl 4 reaches the end of the inclined slot 25. The length and the shape of the inclined slot 25 thus correspond to the amplitude of movement of the lever between its upper position and its lowest position.

The user then releases the lever 1, which rises to its upper position under the effect of a return spring, not shown, integrated on the pawl 4. This upward movement again drives the pawl 4 rearward, and the movement of its end 24 into the following longitudinal slot 26. When this end 24 reaches the end position of this longitudinal slot 26, in the upper position of the lever, it reaches a stable position in this slot, at the bottom of a groove in which a small step 27 prevents any return to the rear. This step 27 in the slot 26 thus performs the non-return function for the bolt 5, while generating a light audible click at the moment the pawl crosses it. It thus represents a third alternative to the two embodiments of non-return devices that will be described below with reference to FIGS. 20 to 27. Thus, subsequent pressing of the lever drives the pawl into the following inclined part 26 of the bolt, once again causing its rotation, as has been explained above. Alternatively, one or more complementary steps could be formed in these slots 25, 26, depending on the application implemented.

Finally, this solution makes it possible to achieve substantially the same result as the first embodiment for example, by replacing the previous ratchet principle with a principle based on cams. Lateral abutments 29 prevent any lateral movement of the pawl 4, which thus moves exclusively in the longitudinal direction. Advantageously, these lateral abutments 29 can be integrated directly in the rear part 2b of the body of the device.

Figure 19:
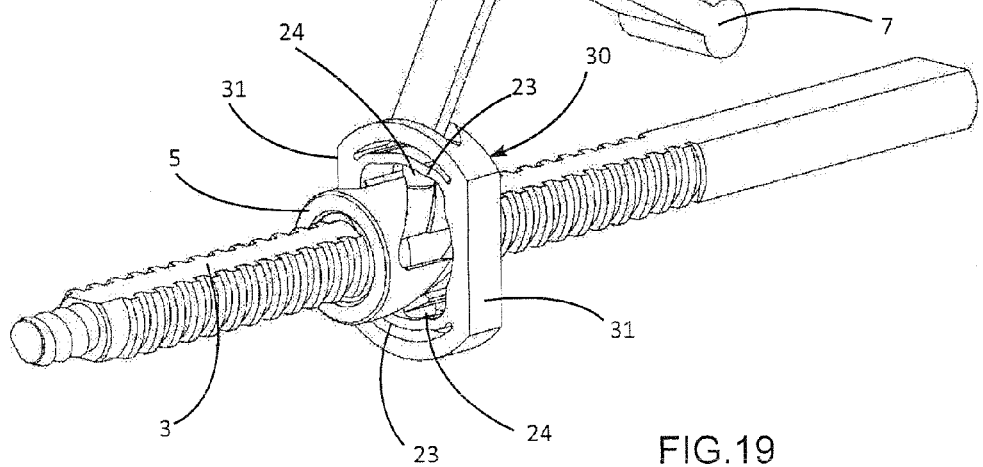
FIG. 19 shows a perspective view of the pusher mechanism of an ejection device according to a variant of the fourth embodiment of the invention.

FIG. 19 illustrates a variant of this fourth embodiment of the invention. In this variant, the bolt is in the same form as above. However, an actuation element 30 for the bolt is arranged at the end of the pawl 4. This actuation element 30 has vertical side parts 31 abutting against the body of the ejection device and thus preventing any lateral movement. It has an inner surface completely surrounding the bolt 5. This surface has two engagement elements 24 positioned on each side of the threaded rod 3. Thus, each of these two engagement elements is positioned symmetrically in slots of the bolt 5, exactly at the same level of a similar slot. In this way, the actuation of the lever drives the pawl 4, which transmits a longitudinal force entraining the rotation of the bolt 5 by way of the actuation element 30. Thus, the two engagement elements of the actuation element 30 move simultaneously and symmetrically inside a slot of the bolt 5, in a manner similar to the movement of the end 24 of the pawl 4 as explained above. This variant has the advantage of greater stability and better transmission of the force from the pawl 4 to the bolt 5 by virtue of two complementary engagement elements. The engagement elements 24 are held at the bottom of the slots of the bolt 5 by an elastic blade 23 of the actuation element 30. Alternatively, the actuation element could comprise more than two engagement elements. Moreover, the actuation element could comprise a spring of the elastic leaf type, similar to the blade 35, in order to promote the return of the engagement elements 24 to the rear during the upward movement of the lever, as a complement to the simple spring effect exerted by the lever.

Finally, the means for controlling the bolt in this fourth embodiment remains simply a pawl, optionally with a special actuation element 30 at its lower end.

FIGS. 20 and 21 show a non-return device in a first embodiment for an ejection device according to the invention, its function being to prevent the rotation of the bolt 5 of the ejection device in the direction counter to that permitting the ejection of the product. These figures show the pawl 4 connected to the lever 1 and acting on the ratchet formed on the periphery of the bolt 5. The pawl 4 comprises a tooth 14 toward its end which acts on a tooth 8 of the bolt 5, as has been explained with reference to FIG. 3. The body of the ejection device comprises a non-return pawl 41, in the form of an elastic blade made of plastic and obtained during the molding of the body of the device. During the actuation of the lever 1, this blade deforms, rubbing against the inclined ramp 39 formed by a tooth 8 of the bolt 5, so as to permit the rotation of the bolt 5 in the direction of ejection of the product. When the lever 1 reaches the end of its travel, the blade forming the non-return pawl 41 reaches the point of the tooth 8, then tilts on the other side of the point against the wall 40 of the tooth 8. This tilting is accompanied by an elastic return of the non-return pawl 41 to its nominal position, generating an audible click from which the user easily identifies the end of this rotation movement of the bolt. He can then release the lever 1, which moves back up automatically to its upper starting position, while at the same time the blade of the non-return pawl 41 remains bearing on the wall 40 of the bolt 5, preventing the rotation of the bolt in the reverse direction.

This rotation could be caused either by the rubbing of the pawl 4 on the bolt 5 during the upward movement of the lever 1 or by the residual pressure of the product to be ejected. The non-return pawl 41 thus performs a safety function and ensures that the next pressure on the lever 1 will indeed permit another controlled advance of the threaded rod by the desired distance, so as to obtain the correct dose of ejected product. This design of the non-return pawl has been described in connection with the first variant of the first embodiment of the ejection device according to the invention. However, it naturally remains compatible with all the other embodiments of the ejection device that have been described above.

FIGS. 22 to 27 show a second embodiment of a non-return device for an ejection device according to the invention. Such a non-return device is based on a cylindrical component 42 provided in the area of the central bore of the rear part 2b, either separate or integrated with the latter, in which the threaded rod 3 is moved and which comprises teeth 43 at one of its ends, which come into engagement with complementary teeth 34 extending in the longitudinal direction of the bolt 5. These teeth 34, 43 have an asymmetrical shape permitting the rotation of the bolt 5 only in the direction of ejection of the product and prevents its rotation in the opposite direction.

During the rotation of the bolt under the effect of the pawl 4, its teeth 34 slide against those 43 of the non-return device, by virtue of inclined parts permitting this sliding. This sliding of the teeth at the same time causes a slight deflection of the bolt 5 in the longitudinal direction, by a distance corresponding to the height of a tooth 43 of the non-return device.

The end of travel of the lever 1 then corresponds to the phase where the points of the teeth 34 of the bolt 5 escape from the teeth 43 of the non-return device and again make contact with the following teeth, the bolt 5 recovering its initial position in the longitudinal direction. This final phase, at the end of movement of the lever 1, is thus accompanied by an audible click which, as in the preceding embodiment, indicates the end of the ejection of the dose of product corresponding to one actuation of the lever.

At its second longitudinal end, opposite from its toothed end 34, the bolt 5 comprises an elastic blade 35, which cooperates with a fixed part 36 provided in the central zone of the body of the ejection device. This elastic blade 35 has the function of returning the bolt to its nominal position in the longitudinal direction in contact with the non-return device. It is compressed against the fixed part 36 of the device when the bolt deflects from its initial position, which generates an elastic force promoting the return of the bolt in the corresponding teeth 43 of the non-return device at the end of the phase of actuation of the lever.

Furthermore, it should be noted that this slight longitudinal movement of the bolt 5 toward the front of the ejection device during the actuation of the lever tends to act on the threaded rod 3 in the sense of increasing the pressure on the product to be ejected. Thus, this effect induces an additional force promoting the ejection of the product, which is especially useful in the case of a particularly pasty product. However, this slight longitudinal movement of the bolt 5 evidently has no influence on the final dose ejected, which depends only on the movement of the threaded rod between its initial position and final position inside the ejection device at the start and end of actuation of the lever, whilst the bolt occupies the same longitudinal positioning in these two end positions of the lever. If appropriate, this movement of the bolt can be damped and compensated by the dimensions and elasticity of the front piston 16.

This second design of a non-return device has been illustrated in connection with the first embodiment of the invention. Alternatively, it remains compatible with the other embodiments of the invention. It can also have other forms. For example, FIGS. 11 to 13 represent the implementation of this design on the second embodiment of the invention, with a slight variation in that the teeth 43 of the non-return device engage with an elastic blade whose end forms a tooth of the bolt 5.

Of course, the invention is not limited to the embodiments that have been described by way of example. It is possible to imagine other implementations of the concept of the invention involving the combinations of the above embodiments or equivalent features. In particular, the means of controlling the threaded rod from the lever can be obtained differently, by a pawl of an entirely different shape, not necessarily in the form of a one-piece shaft-shaped component, and/or the teeth used for the different designs can have different geometries and/or orientations, there can be many gears of diverse shapes, the bolt can have any other shape, etc. The pusher mechanism based on a bolt and threaded rod can be obtained by a plastic injection method, by which most of the elements of the ejection device can be produced easily and made recyclable. The body of the ejection device can have other geometries.

Provision could be made for the lever to be manipulated in such a way as to generate the passage of several teeth and audible clicks, that is to say the ejection of several minimal doses, during a single actuation. Thus, its actuation could then be partial, not necessarily covering its entire amplitude of possible rotation, while functioning according to the principle explained above.

Finally, the solution according to the invention affords the following advantages:
- it permits perfectly controlled ejection of small doses of product;
- it permits a simple and inexpensive mechanism compatible with the one-off use of a disposable injection device, of which all the component parts are recyclable;
- it combines a simple design comprising several plastic parts that can be produced by injection, including a movable lever on a main body, and a simple rotation mechanism allowing great precision to be achieved without significantly increasing the complexity of the device.

The invention claimed is:

1. A device for ejecting a liquid or pasty product, comprising
   a body having a recess for receiving a product to be ejected,
   a threaded rod disposed in a bore of the body, the threaded rod movable in translation to act on the product to be ejected and having a substantially cylindrical shape with a surface in the translation direction truncated in order to prevent rotation of the thread rod by engagement with a corresponding shape of the bore in the body;
   a bolt, mounted in engagement with the threaded rod to cause the threaded rod to move in translation,
   a lever, which acts on the bolt by way of a control means for causing the rotation of the bolt when the lever is pressed, and
   a non-return means connected to the body of the device and in engagement with the bolt, to prevent reverse rotation of the bolt when the lever is released,
   wherein the non-return device is fixed with respect to the body and comprises an elastic blade that is in flexible engagement with the bolt, the blade deformable from a nominal position to enable rotation of the bolt when the lever is pressed and returnable to the nominal position to prevent rotation of the bolt when the lever is released,
   wherein an end of the threaded rod is adapted to engage with a pusher piston enabled to act on the liquid or pastry product.

2. The device for ejecting a liquid or pasty product as claimed in claim 1 wherein the control means comprises a pawl connected to the lever.

3. The device for ejecting a liquid or pasty product as claimed in claim 2 wherein the lever is mounted for rotation or flexion about an axis in the rear part of the lever.

4. The device for ejecting a liquid or pasty product as claimed in claim 3 wherein the lever comprises an axle at a rear end of the lever, and a means for rotatably mounting the axle on the body.

5. The device for ejecting a liquid or pasty product as claimed in claim 2 wherein the lever and the pawl form the same molded plastic component.

6. The device for ejecting a liquid or pasty product as claimed in claim 2 wherein the bolt comprises teeth or slots on an outer peripheral surface engaging directly or indirectly with the pawl, the profile of the teeth extending in a vertical transverse plane (yz) and/or in a vertical longitudinal plane (xz) of the bolt.

7. The device for ejecting a liquid or pasty product as claimed in claim 2 wherein the pawl is in the form of a shaft connected to the lever at a first end, forming an elastically or non-elastically movable shaft, and a second end able to engage with teeth of a ratchet, the second end being rectangular or the second end having one or more teeth toward this second end, or the second end comprising a rounded part able to engage with a slot.

8. The device for ejecting a liquid or pasty product as claimed in claim 2 comprising a ratchet mounted in rotation about the threaded rod, the ratchet having two or more teeth that are arranged on an outer peripheral surface thereof and of which a profile of the ratchet extends in a vertical transverse plane (yz) in to engage with the pawl, and comprising at least one tooth oriented in a longitudinal direction in to engage with the bolt to drive the bolt in rotation during the actuation of the lever.

9. The device for ejecting a liquid or pasty product as claimed in claim 7 wherein the bolt includes teeth on an outer peripheral surface engaging directly or indirectly with the pawl, the teeth of the bolt or of the ratchet have a pointed profile and are asymmetrical or have a rectangular, conical or trapezoid symmetrical profile.

10. The device for ejecting a liquid or pasty product as claimed in claim 1 wherein the control means comprises one or more intermediate gears for gearing down transmission of the speed of rotation to the bolt.

11. The device for ejecting a liquid or pasty product as claimed in claim 1 wherein the bolt comprises an alternating sequence of inclined slots and longitudinal slots formed on an outer cylindrical surface of the bolt.

12. The device for ejecting a liquid or pasty product as claimed in claim 1 comprising a pawl connected to the lever, one end of the pawl engages with slots in the bolt, and/or the pawl comprises at one end, an actuation element comprising several engagement elements engaging with the slots of the bolt to cause the bolt to rotate during actuation of the lever.

13. A device for ejecting a liquid or pasty product, comprising: a body having a recess for receiving a product to be ejected, a threaded rod disposed in a bore of the body, the threaded rod movable in translation to act on the product to be ejected and having a substantially cylindrical shape with a surface in the translation direction truncated to prevent rotation of the threaded rod by engagement with a corresponding shape of the bore in the body;

a bolt, mounted in engagement with the threaded rod to cause the threaded rod to move in translation, a lever, which acts on the bolt by way of a control means for causing the rotation of the bolt when the lever is pressed, and a non-return means connected to the body of the device and in engagement with the bolt, to prevent reverse rotation of the bolt when the lever is released, wherein the non-return device comprises a cylindrical component formed in the area of the bore in which the threaded rod moves, the non-return device having teeth which extend in a longitudinal direction at one end and which come into engagement with at least one complementary tooth extending in a longitudinal direction of the bolt.

14. The device for ejecting a liquid or pasty product as claimed in claim 1 comprising a means for emitting an audible click when a minimal dose is ejected by the actuation of the lever.

15. The device for ejecting a liquid or pasty product as claimed in claim 1 comprising a body having a front part to contain the product to be ejected, and a rear part, in which the bolt is located.

16. The device for ejecting a liquid or pasty product as claimed in claim 15 comprising:

at least one tool holder arranged in the front part of the body of the ejection device and/or a tool holder arranged in the front part of the body of the ejection device; and a locking means of the Luer lock type for locking the tool holder on the ejection device.

\* \* \* \* \*